US008043226B2

United States Patent
Kim et al.

(10) Patent No.: US 8,043,226 B2
(45) Date of Patent: Oct. 25, 2011

(54) APPARATUS AND METHOD FOR SIMULTANEOUSLY MEASURING BIO SIGNALS

(75) Inventors: Youn-ho Kim, Hwaseong-si (KR); Sang-kon Bae, Seoul (KR); Kyung-ho Kim, Yongin-si (KR); Hong-sig Kim, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 12/813,835

(22) Filed: Jun. 11, 2010

(65) Prior Publication Data

US 2010/0249537 A1 Sep. 30, 2010

Related U.S. Application Data

(62) Division of application No. 11/090,051, filed on Mar. 28, 2005, now Pat. No. 7,758,513.

(30) Foreign Application Priority Data

Mar. 27, 2004 (KR) .................. 10-2004-0021034
Mar. 22, 2005 (KR) .................. 10-2005-0023489

(51) Int. Cl.
*A61B 5/05* (2006.01)

(52) U.S. Cl. ........................................ 600/554
(58) Field of Classification Search ............... 607/9, 18; 600/509, 510, 513, 554, 306, 319, 323, 324, 600/326, 334, 336, 412, 455, 456, 465, 468, 600/474, 483, 484, 529, 544, 546
See application file for complete search history.

(56) References Cited

U.S. PATENT DOCUMENTS

| | | | |
|---|---|---|---|
| 5,910,156 A * | 6/1999 | Cinbis et al. | .............. 607/27 |
| 6,936,012 B2 | 8/2005 | Wells | |
| 7,020,507 B2 | 3/2006 | Scharf et al. | |
| 7,079,880 B2 | 7/2006 | Stetson | |
| 2002/0028998 A1 | 3/2002 | Chesney et al. | |
| 2002/0077536 A1 | 6/2002 | Diab et al. | |
| 2002/0128544 A1 | 9/2002 | Diab et al. | |
| 2002/0183794 A1 | 12/2002 | Struble | |
| 2003/0004548 A1 | 1/2003 | Warkentin | |
| 2003/0032889 A1 | 2/2003 | Wells | |
| 2003/0036689 A1 | 2/2003 | Diab et al. | |
| 2003/0097049 A1 | 5/2003 | Diab et al. | |
| 2003/0216788 A1 | 11/2003 | Perschbacher et al. | |
| 2004/0049235 A1 | 3/2004 | Deno et al. | |
| 2004/0230128 A1 | 11/2004 | Brockway et al. | |
| 2004/0230129 A1 | 11/2004 | Haefner | |

(Continued)

FOREIGN PATENT DOCUMENTS

JP 50-125287 3/1974

(Continued)

*Primary Examiner* — Carl H Layno
*Assistant Examiner* — Allen Porter, Jr.
(74) *Attorney, Agent, or Firm* — Sughrue Mion, PLLC

(57) ABSTRACT

An apparatus and method for simultaneously measuring at least two different bio signals without interference are provided. The apparatus includes a stimulus signal generating unit generating the stimulus signal to be applied to a human body, a sensing unit contacting the human body, including a plurality of electrodes to which the stimulus signal is applied and from which at least one intermediate signal containing the first and second bio signals is detected, configured to share at least one of the plurality of electrodes to apply the stimulus signal or to detect each intermediate signal, and a signal acquisition unit separating and acquiring the first and second bio signals from each intermediate signal detected from the sensing unit.

20 Claims, 8 Drawing Sheets

U.S. PATENT DOCUMENTS

| | | |
|---|---|---|
| 2004/0230245 A1 | 11/2004 | Prutchi et al. |
| 2004/0230249 A1 | 11/2004 | Haefner |
| 2004/0254616 A1 | 12/2004 | Rossing et al. |
| 2004/0260186 A1 | 12/2004 | Dekker |
| 2005/0096517 A1 | 5/2005 | Diab et al. |
| 2005/0119708 A1 | 6/2005 | Haefner |

FOREIGN PATENT DOCUMENTS

| | | |
|---|---|---|
| JP | 52-80689 | 7/1977 |
| JP | 61-45733 A | 3/1986 |
| JP | 61-232832 A | 10/1986 |
| JP | 11-347007 A | 12/1999 |

* cited by examiner

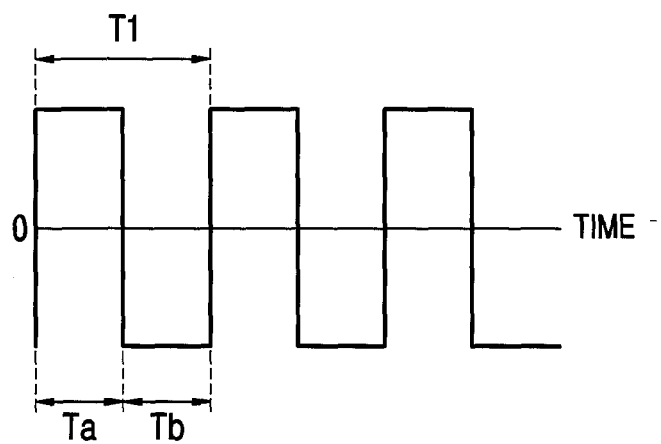
FIG. 4A
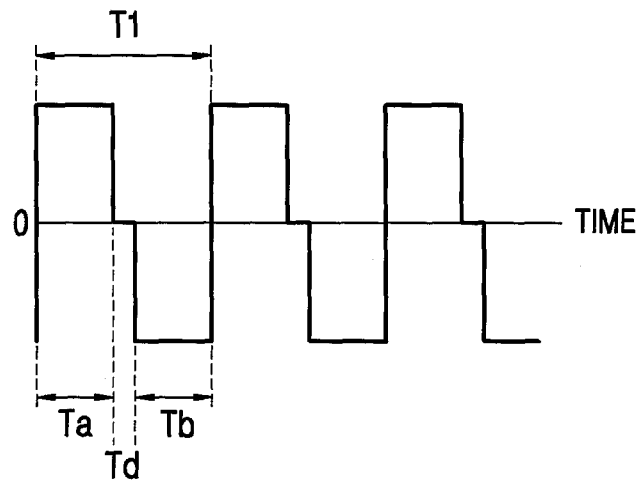
FIG. 4B
FIG. 5
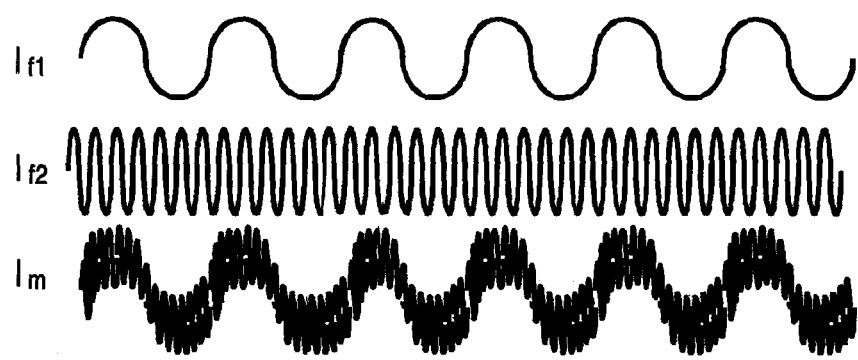

APPARATUS AND METHOD FOR SIMULTANEOUSLY MEASURING BIO SIGNALS

CROSS-REFERENCE TO RELATED PATENT APPLICATION

This is a Divisional of application Ser. No. 11/090,051, now U.S. Pat. No. 7,758,513, filed on Mar. 28, 2005, which claims priority from Korean Patent Application No. 10-2004-0021034, filed on Mar. 27, 2004 in the Korean Intellectual Property Office, and Korean Patent Application No. 10-2005-0023489, filed on Mar. 22, 2005 in the Korean Intellectual Property Office, the disclosures of which are incorporated herein in their entirety by reference.

BACKGROUND OF THE INVENTION

1. Field of the Invention

Apparatuses and methods consistent with the present invention relate to bio signal measuring, and more particularly, to simultaneously measuring at least two different bio signals without interference.

2. Description of the Related Art

The health condition of a patient can be determined by measuring various bio signals to detect abnormal health symptoms. Commonly, a patient visits a doctor's office and the doctor utilizes medical instruments for measuring bio signals precisely. Recently, to reduce the inconvenience of visiting the doctor's office, research on remote medical treatment has been carried out. Various types of instruments for remotely measuring bio signals have been put on the market. However, if a patient is unskilled, the accuracy of the bio signal measurement is limited. Furthermore, since a plurality of measurement instruments should be purchased to measure many kinds of bio signals, the costs that a patient should pay are very high.

In a conventional bio signal measuring apparatus, sensors for sensing bio signals are connected in an octopus shape to a main body of the apparatus. A user connects by wire or wirelessly bio signal measurement modules, such as a sphygmomanometer, a weight meter, and/or a $SpO_2$ meter, to the main body of the apparatus. After this, items to be measured are selected from a key panel by the user. However, a measurement item should be selected for every measurement, and a measurement mode should be changed for each item. This is troublesome, and the time required for the measurement is increased. Furthermore, since the measurement modules should be connected to the main body, the system is complicated, and thus the costs for implementing the entire system are increased.

Other examples of conventional technologies for bio signal measurement are disclosed in U.S. Pat. No. 5,152,296 and Korean Patent Publication No. 2001-0096186. In U.S. Pat. No. 5,152,296, various sensors are integrated into one sensor module for measuring more items, such as electrocardiogram (ECG), $SpO_2$, and blood pressure signals. This architecture can increase the convenience of measurement in that various bio signals can be measured in one measurement operation. However, since sensors for each measurement item should be separately prepared, costs are still increased, and kinds of measurement items are limited due to spatial constraints of the sensor module. An integrated medical diagnosis apparatus disclosed in Korean Patent Publication No. 2001-0096186 includes a sensor unit constituted by integrating a plurality of sensors for detecting bio signals of a patient and a module unit including changeable and pluggable medical instruments desired by the patient by modularizing a plurality of medical instruments for measuring information corresponding to the bio signals detected by the sensor unit. The apparatus further includes a rear case in which the sensor unit is formed with an external recess. By integrating the sensors for measuring bio signals and modularizing devices for collecting the bio signals measured by the sensors, the user can easily measure his/her bio signals. However, in this case, since the bio signals to be measured are sequentially measured using a selecting switch, the time required for measurement is longer, and it is difficult to simultaneously measure various bio signals at the same time.

Methods of measuring bio signals are largely divided into two categories. First, bio signals naturally generated inside a human body, such as ECG, body temperature, respiration, and pulse, can be directly measured using electrodes. The ECG can be measured using a potential difference between two electrodes contacting the human body, e.g., two electrodes contacting a right end and a left end centering the heart. Second, bio signals, such as body fat, skin resistance, and the amount of blood flow, can be measured by applying a stimulus signal from the outside and receiving a signal responding to the stimulus signal. For example, for the body fat, a stimulus signal is applied through the electrodes contacting both ends, and signals detected from the same electrode or different electrodes are measured, and for the skin resistance, a stimulus signal is applied through an electrode contacting the left end, and a signal detected from the same electrode contacting the left end in response to the stimulus is measured. For signals that can be applied as the stimulus signal, light of a wavelength sensitively responding to each bio signal or a constant alternative current of an optimized frequency for each bio signal can be used. For example, the body fat is optimized to a certain frequency of tens of kHz, and the skin resistance is optimized to a certain frequency between 20 Hz and 50 Hz.

Interference between first and second bio signals does not occur in a case where measurement paths are different when two bio signals having different physical mechanisms are simultaneously measured, e.g., in a case where the first bio signal naturally generated is measured while the second bio signal is measured by irradiating light. However, in a case where the measurement paths are all the same, e.g., in a case where the first bio signal is measured while the second bio signal is measured by applying a current, the measurement cannot be correctly achieved due to the interference between the first and second bio signals.

SUMMARY OF THE INVENTION

The present invention provides an apparatus and method for simultaneously measuring at least two different bio signals without interference.

According to an aspect of the present invention, there is provided a bio signal measurement apparatus for simultaneously measuring a first bio signal generated in response to a stimulus signal and a second bio signal naturally generated, the apparatus comprising: a stimulus signal generating unit generating the stimulus signal to be applied to a human body; a sensing unit contacting the human body, including a plurality of electrodes to which the stimulus signal is applied and from which at least one intermediate signal containing the first and second bio signals is detected, configured to share at least one of the plurality of electrodes to apply the stimulus signal or to detect each intermediate signal; and a signal acquisition unit separating and acquiring the first and second bio signals from each intermediate signal detected from the sensing unit.

According to another aspect of the present invention, there is provided a bio signal measurement method of simultaneously measuring a first bio signal generated in response to a stimulus signal and a second bio signal naturally generated, the method comprising: providing a sensing unit contacting a human body, including a plurality of electrodes to which the stimulus signal is applied and from which at least one intermediate signal containing the first and second bio signals is detected, configured to share at least one of the plurality of electrodes to apply the stimulus signal or to detect each intermediate signal; generating the stimulus signal to be applied to the human body; and separating and acquiring the first and second bio signals from each intermediate signal detected from the sensing unit.

According to still another aspect of the present invention, there is provided a computer-readable recording medium having recorded thereon a computer-readable program for performing the above method.

BRIEF DESCRIPTION OF THE DRAWINGS

The above and other aspects of the present invention will become more apparent by describing in detail exemplary embodiments thereof with reference to the attached drawings in which:

FIGS. 4A and 4B show examples of a temporal separating method adopted in a first and a second temporal separating units shown in FIGS. 1 through 3;

FIG. 5 is an example of combining two alternate currents in a combining unit shown in FIG. 3;

DETAILED DESCRIPTION OF EXEMPLARY EMBODIMENTS OF THE INVENTION

Hereinafter, exemplary embodiments of the present invention will now be described in detail with reference to the accompanying drawings.

First, a bio signal generated in response to a stimulus signal is called a first bio signal, and a bio signal naturally generated is called a second bio signal. In the present invention, a sensing unit (130 of FIG. 1) contacting a human body comprises a plurality of electrodes to which the stimulus signal is applied and from which an intermediate signal containing the first and second bio signals is detected. Particularly, the sensing unit is configured to share at least one of the plurality of electrodes to detect each intermediate signal. In addition, a signal acquisition unit (160 of FIG. 1) separates and acquires the first and second bio signals from each intermediate signal detected from the sensing unit, by using at least one of a temporal separation and an electric separation. The temporal separation may be used irrespective of frequency bands in which each of the first and second bio signal to be simultaneously measured exists, since signals are temporally separated. However, the performance of the temporal separation is closely related to the processing speed of a controller (110 of FIG. 1). Therefore, if items to be simultaneously measured increase and a low-level controller is used, it is difficult to guarantee the performance. The electric separation may separate signals by means of a combination of a filtering unit and an isolating unit, for obtaining signals of a desired frequency band from an intermediate signal detected from the sensing unit. However, the electric separation can be used just when frequency bands in which each of the first and second bio signal to be simultaneously measured exists are separated from each other.

Figure 1:
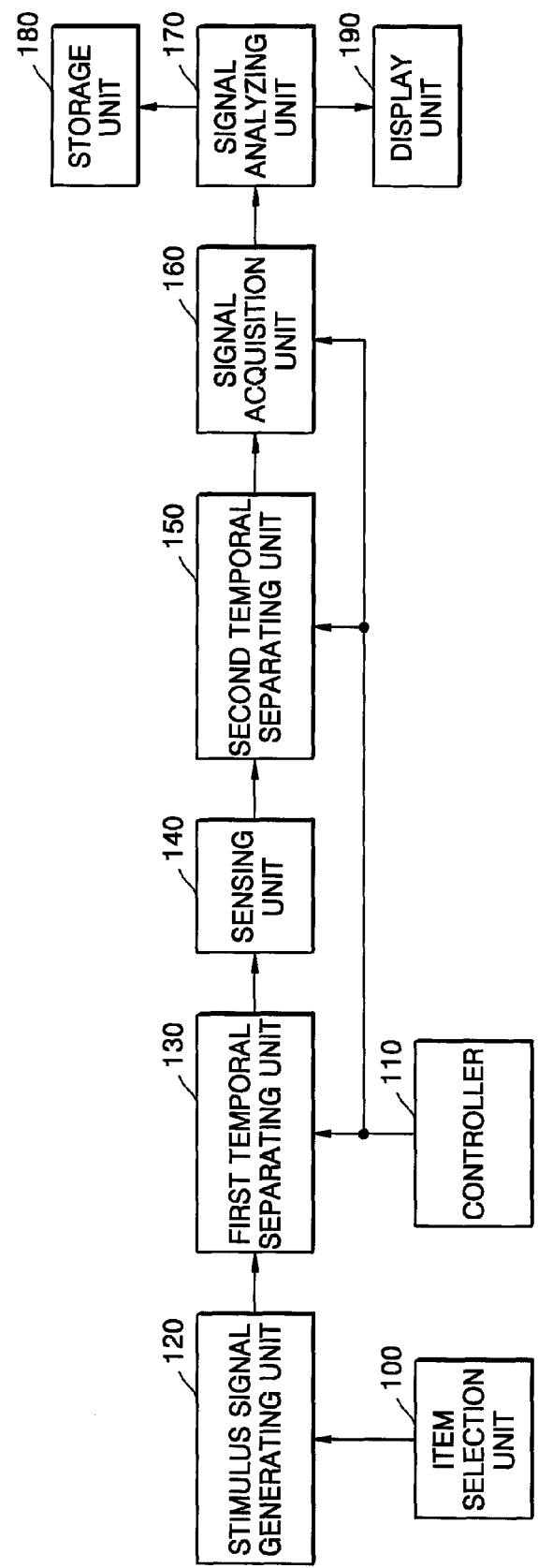
FIG. 1 is a schematic block diagram of a bio signal measurement apparatus according to a first exemplary embodiment of the present invention.

FIG. 1 is a schematic block diagram of a bio signal measurement apparatus according to a first exemplary embodiment of the present invention, which measures the first and second bio signals using the temporal separation. The apparatus includes an item selection unit 100, a controller 110, a stimulus signal generating unit 120, a first temporal separating unit 130, a sensing unit 140, a second temporal separating unit 150, a signal acquisition unit 160, a signal analyzing unit 170, a storage unit 180, and a display unit 190. The item selection unit 100 may be optionally included.

Referring to FIG. 1, the item selection unit 100 selects bio signals, which a user desires to simultaneously measure. The user can select at least one of various first bio signals and at least one of various second bio signals. In another exemplary embodiment, the item selection unit 100 selects at least one bio signal, which a user desires not to simultaneously measure, among a plurality of items set in advance.

The controller 110 generates a control signal to switch a first and a second temporal separating units 130 and 150 in a constant time interval for preventing the interference between the first and second bio signals to be simultaneously measured. For example, the controller 110 divides an entire time T required for simultaneously measuring the first and second bio signals into very short sampling periods of a pulse signal, as shown in FIGS. 4A and 4B. In FIGS. 4A and 4B, a first interval (Ta) is used to apply the stimulus signal to the sensing unit (140) and to measure the first bio signal and a second interval (Tb) is used to measure the second bio signal.

The stimulus signal generating unit 120 generates a stimulus signal best responding to a human body to be applied to the first temporal separating unit 130, with regard to each first bio signal. For example, if the first bio signal is a body fat signal, an alternate current (AC) having a certain frequency of tens of kHz is used as the stimulus signal, and if the first bio signal is a skin resistance signal, an AC optimized to a certain frequency between 20 Hz and 50 Hz is used as the stimulus signal. Also, the stimulus signal generating unit 120 stores stimulus signals mapped to each of the first bio signals. Accordingly, if a user selects items to be simultaneously measured, corresponding stimulus signals are applied to the first temporal separating unit 130. If two or more first bio signals are selected, stimulus signals corresponding to each of first bio signals are generated and the stimulus signals are combined to then be applied to the first temporal separating unit 130.

The first temporal separating unit 130 operates in response to the control signal provided from the controller 110 and prevents interference caused by the stimulus signal during the measurement of the second bio signal. According to this, the stimulus signal is applied to the sensing unit 140 in a constant time interval.

The sensing unit 140 includes a plurality of electrodes attachable to a human body, to which the stimulus signal is applied and from which at least one intermediate signal containing the first and second bio signals is detected. The sensing unit 140 is configured to share at least one of the plurality of electrodes to apply the stimulus signal or to detect each intermediate signal. In an exemplary embodiment, the sensing unit 140 includes four electrodes, i.e., two electrodes for each of the left and right palms. In another exemplary embodiment, the sensing unit 140 includes two electrodes, i.e., one electrode for each of the left and right palms. Any region other than the left and right palms may be used if the first or the second bio signal can be detected in the region. With regard to the first bio signals, the stimulus signal is applied to at least two of the plurality of electrodes and an intermediate signal detected from at least two of the plurality of electrodes is used to measure the first bio signals. With regard to the second bio signals, an intermediate signal detected from at least two of the plurality of electrodes is used to measure the second bio signals.

The second temporal separating unit 150 operates in response to the control signal provided from the controller 110 and prevents interference caused by the first or second bio signal during obtaining the first and second bio signals in the signal acquisition unit 160. According to this, each of a first intermediate signal and a second intermediate signal is detected from the plurality of electrodes included in the sensing unit 140 in a constant time interval. The second temporal separating unit 150 operates in synchronization with the first temporal separating unit 130 and both may be implemented using an analog switch.

The signal acquisition unit 160 operates depending on the control signal provided from the controller 110, and separates and acquires the first and second bio signals from the first and second intermediate signals detected from the sensing unit 140 in a constant time interval depending on the operation of the second temporal separating unit 150. If there are a plurality of the first bio signals to be simultaneously measured and stimulus signal having a frequency corresponding to each first bio signal are applied to the sensing unit 140, a corresponding first bio signal can be obtained using each frequency.

The signal analyzing unit 170 analyzes the first and second bio signals acquired by the signal acquisition unit 160 and obtains corresponding data. For example, data corresponding to the first bio signal such as the body fat or the skin resistance is measured using impedance obtained from voltage difference between two electrodes and the second bio signal such as the ECG can be obtained from potential difference obtained using at least two electrodes.

The data corresponding to the first and second bio signals obtained as the analysis results of the signal analyzing unit 170 is stored in the storage unit 180 or displayed on the display unit 190.

Figure 2:
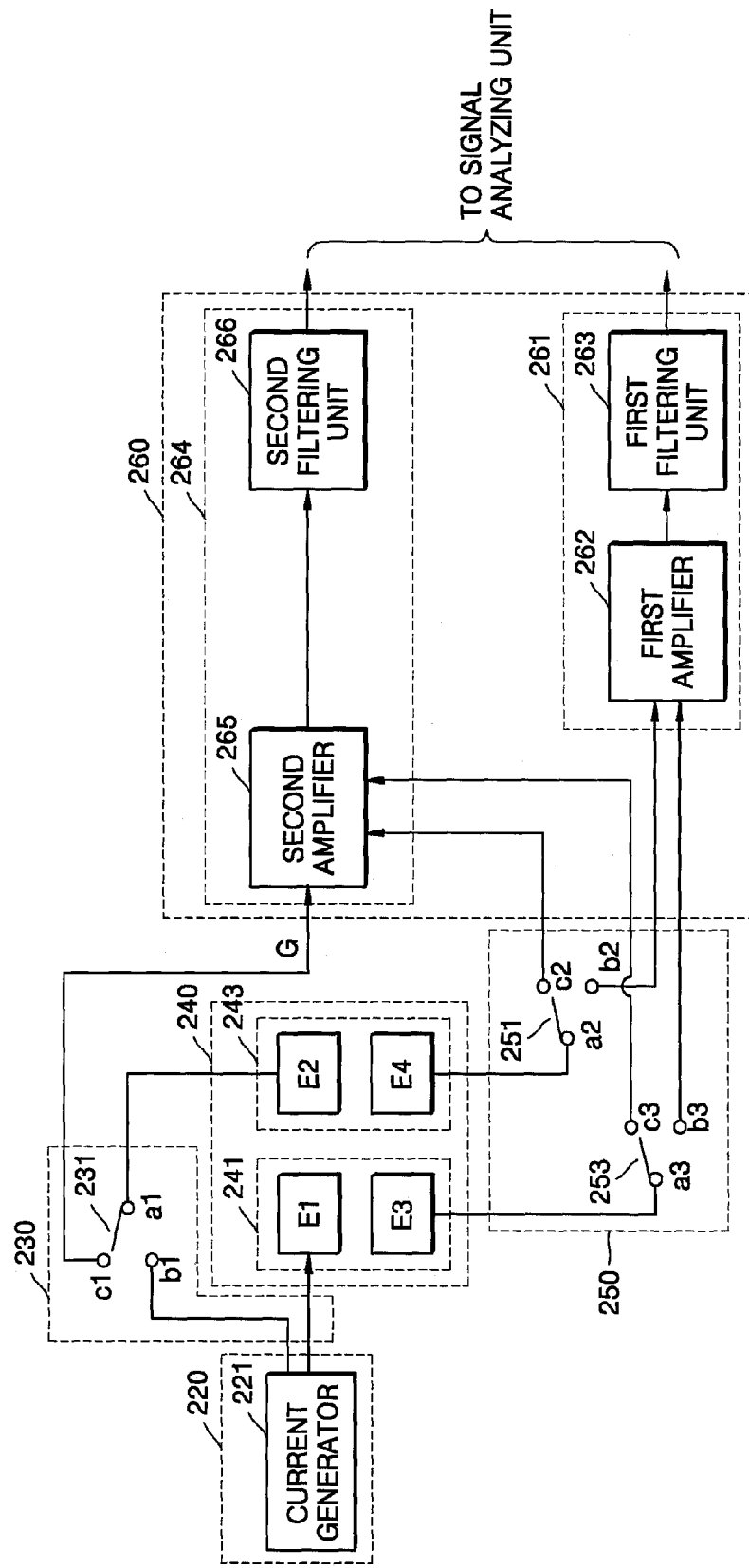
FIG. 2 is an exemplary detailed block diagram of the bio signal measurement apparatus shown in FIG. 1.

FIG. 2 is an exemplary detailed block diagram of the bio signal measurement apparatus shown in FIG. 1.

In the bio signal measurement apparatus shown in FIG. 2, one measurement item of the second bio signals is selected or measured. Referring to FIG. 2, a stimulus signal generating unit 220 includes a first current generator 221, and a first temporal separating unit 230 includes a first switch 231. A sensing unit 240 includes a first electrode group 241 including first and third electrodes E1 and E3 and a second electrode group 242 including second and fourth electrodes E2 and E4.

A second temporal separating unit 250 includes a second switch 251 and a third switch 253. A signal acquisition unit 260 includes a first acquisition unit 261 and a second acquisition unit 264. The first acquisition unit 261 includes a first amplifier 262 and a first filtering unit 263, and the second acquisition unit 264 includes a second amplifier 265 and a second filtering unit 266.

For the convenience of description, a body fat signal or a skin resistance signal is an example of the first bio signals generated in response to an applied current and an ECG signal is used as an example of the naturally generated second bio signals.

The ECG signal is generated by an electrical activity of the heart and detected using potential difference(s) detected from at least two positions apart from the heart. The potential differences vary according to distances from the heart. Thus, in the present exemplary embodiment, the palms are used as an example of the measurement positions. In order to measure the ECG, in the sensing unit 240, three electrodes e.g., the second through fourth electrodes E2, E3 and E4 or two electrodes e.g., the third and fourth electrodes E3 and E4. The body fat is measured using resistance values detected from both ends of the human body according to the amount of body fat. That is, a constant AC is applied and then a potential difference between two electrodes is converted to a resistance value. Here, for a frequency of the AC, a frequency which responds well to the body fat component in the human body, e.g., 50 kHz, is used. When two electrodes are used for measuring the body fat, the AC is applied to the first and second electrodes E1 and E2, and then an AC voltage between the first and second electrodes E1 and E2 is measured. When four electrodes are used for measuring the body fat, the AC is applied to the first and second electrodes E1 and E2, and then an AC voltage between the third and fourth electrodes E3 and E4 is measured. The measured AC voltage is converted to impedance. In the present exemplary embodiment, four electrodes are used. If sweat comes out from the skin in accordance with a change in the autonomic nervous system, a resistance value of the surface of the skin varies. For a frequency of the AC, a frequency well responding to the skin resistance, e.g., a certain frequency between 20 Hz and 50 Hz, is used. In order to measure the skin resistance, the AC is applied to the first and third electrodes E1 and E3, and then an AC voltage between the first and third electrodes E1 and E3 is measured. The measured AC voltage is converted to a resistance value.

An operation of the present exemplary embodiment will now be described based on the bio signal measurement principle.

Referring to FIG. 2, the first current generator 221 generates an AC having a frequency corresponding to each of the first bio signals. That is, the first current generator 221 generates the AC ($I_{f2}$ of FIG. 5) having the frequency of 50 kHz if the body fat is the second bio signal.

The first switch 231 performs a switching operation depending on the control signal from the controller 110. The first switch 231 connects a contact point a1 to a contact point b1 in a Ta period (refer to FIGS. 4A and 4B) for measuring a first bio signal. In a Tb period (refer to FIGS. 4A and 4B) for measuring a second bio signal, the first switch 231 connects the contact point a1 to a contact point c1. Accordingly, the AC provided by the first current generator 221 is not applied to the second electrode E2 of the sensing unit 240 in the Tb period, and the AC provided by the first current generator 221 is applied to the second electrode E2 of the sensing unit 240 in the Ta period. Even if the AC provided by the first current generator 221 is always applied to the first electrode E1 of the sensing unit 240 regardless to periods, since the AC is not applied to the second electrode E2 of the sensing unit 240 in the Tb period, a current loop is not formed. Thus no interference occurs when the second bio signal is measured in the Tb period.

The second and third switches 251 and 253 performs a switching operation in synchronization with the first switch 231 depending on the control signal from the controller 110. In the Ta period (refer to FIGS. 4A and 4B) for measuring a first bio signal, a contact point a2 of the second switch 251 is connected to a contact point b2, and a contact point a3 of the third switch 253 is connected to a contact point b3. In the Tb period (refer to FIGS. 4A and 4B) for measuring a second bio signal, the contact point a2 of the second switch 251 is connected to a contact point c2, and the contact point a3 of the third switch 253 is connected to a contact point c3. Accordingly, voltages detected from the third and fourth electrodes E3 and E4 of the sensing unit 240 if the first bio signal is the body fat are provided to the first acquisition unit 261 included in the signal acquisition unit 260 in the Ta period. In addition, voltages detected from the third and fourth electrodes E3 and E4 of the sensing unit 240 are provided to the second acquisition unit 264 included in the signal acquisition unit 260 in the Tb period.

In the first acquisition unit 261, the first amplifier 262 amplifies the AC voltage between the third and fourth electrodes E3 and E4 connected through the second and third switches 251 and 253 in every Ta period and provides the amplified AC voltage to the first filtering unit 263. The first filtering unit 263 cancels noise components by filtering the amplified AC voltage provided from the first amplifier 262 and provides the noise-cancelled AC voltage to the signal analyzing unit (170 of FIG. 1). In the second acquisition unit 264, the second amplifier 265 sets the second electrode E2 connected through the first switch 231 in every Tb period as a right leg driver of the ECG, differentially amplifies a difference, i.e., a potential difference signal, between the voltages of the third and fourth electrodes E3 and E4 connected through the second and third switches 251 and 253, and provides the differentially amplified potential difference signal to the second filtering unit 266. The second filtering unit 266 cancels noise components by filtering the amplified potential difference signal provided from the second amplifier 265 and provides the noise-cancelled potential difference signal to the signal analyzing unit (170 of FIG. 1).

In a case that there is a demand of measuring the skin resistance instead of the body fat, it may be easily implemented by modifying the connection relation between the sensing unit 240 and the signal acquisition unit 260.

Figure 3:
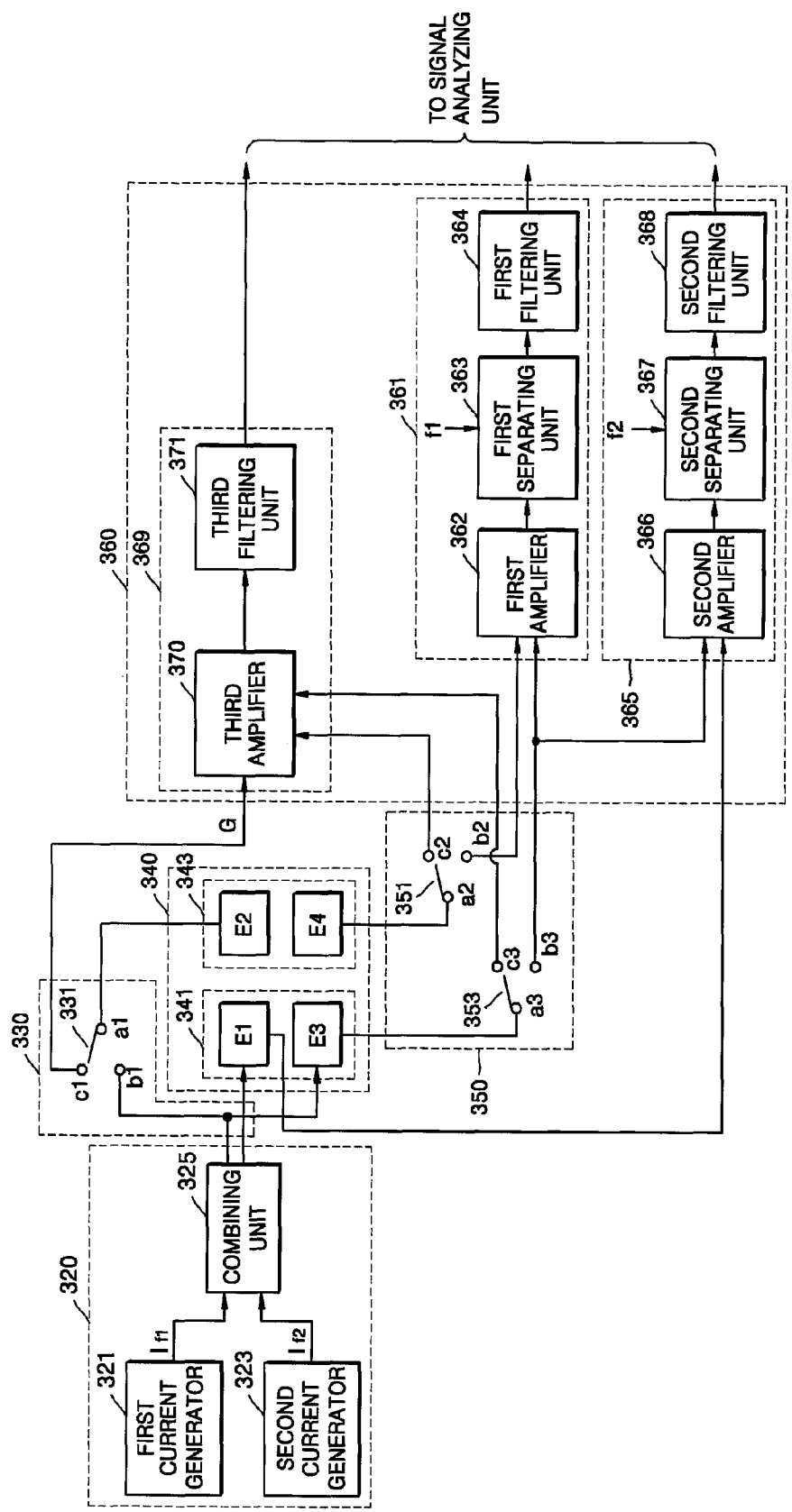
FIG. 3 is another exemplary detailed block diagram of the bio signal measurement apparatus shown in FIG. 1.

FIG. 3 is another exemplary detailed block diagram of the bio signal measurement apparatus shown in FIG. 1.

Referring to FIG. 3, a stimulus signal generating unit 320 includes a first and a second current generator 321 and 323 and a combining unit 325, and a signal acquisition unit 360 includes a first acquisition unit 361, a second acquisition unit 365, and a third acquisition unit 369. The first acquisition unit 361 includes a first amplifier 362, a first separating unit 363 and a first filtering unit 364, the second acquisition unit 365 includes a second amplifier 366, a second separating unit 367 and a second filtering unit 368, and the third acquisition unit 369 includes a third amplifier 370 and a third filtering unit 371. The detailed description of the parts which are the same as those in the apparatus shown in FIG. 2 will be omitted and the different parts will be mainly described.

Referring to FIG. 3, the first and second current generators 321 and 323 generate ACs having a frequency corresponding to each of the two first bio signals. For example, the first current generator 321 generates a first AC ($I_{f1}$ of FIG. 5) having a first frequency f1 between 20 Hz and 50 Hz for measuring the skin resistance and the second current generator 323 generates a second AC ($I_{f2}$ of FIG. 5) having a second frequency f2 of 50 kHz for measuring the body fat. The combining unit 325 generates a combined AC ($I_m$ of FIG. 5) by combining the first and second ACs $I_{f1}$ and $I_{f2}$ generated by the first and second current generators 321 and 323 and provides the combined AC to the first temporal separating unit 330. If one first bio signal other than the skin resistance and the body fat is additionally measured, a third AC is generated to then be combined with the first and second ACs and the combined AC to the first temporal separating unit 330.

In the first acquisition unit 361, the first amplifier 362 amplifies the AC voltage between the third and fourth electrodes E3 and E4 connected through the second and third switches 351 and 353 in every Ta period and provides the amplified AC voltage to the first separating unit 363. The first separating unit 363 separates a portion corresponding to the first frequency component f1 from the amplified AC voltage. The first filtering unit 364 cancels noise components by filtering the AC voltage having the first frequency component f1 separated from the first separating unit 363 and provides the noise-cancelled AC voltage to the signal analyzing unit (170 of FIG. 1).

In the second acquisition unit 365, the second amplifier 366 amplifies the AC voltage between the third and fourth electrodes E3 and E4 connected through the second and third switches 351 and 353 in every Ta period and provides the amplified AC voltage to the second separating unit 367. The second separating unit 367 separates a portion corresponding to the second frequency component f2 from the amplified AC voltage. The second filtering unit 368 cancels noise components by filtering the AC voltage having the second frequency component f2 separated from the second separating unit 367 and provides the noise-cancelled AC voltage to the signal analyzing unit (170 of FIG. 1).

In the third acquisition unit 369, the third amplifier 370 sets the second electrode E2 connected through the first switch 231 in every Tb period as a right leg driver of the ECG, differentially amplifies a difference, i.e., a potential difference signal, between the voltages of the third and fourth electrodes E3 and E4 connected through the second and third switches 251 and 253, and provides the differentially amplified potential difference signal to the third filtering unit 371. The third filtering unit 371 cancels noise components by filtering the amplified potential difference signal provided from the third amplifier 370 and provides the noise-cancelled potential difference signal to the signal analyzing unit (170 of FIG. 1).

Here, if the number of the first bio signals to be simultaneously measured is m (m is an integer equal to or greater than 2) and the total of bio signals to be simultaneously measured including the second bio signal is n, apparatuses shown in FIGS. 2 and 3 may be modified as follows.

First, for the apparatus of FIG. 2, a switching operation of the first and second temporal separating units 230 and 250 is performed n times within one sampling period T1 and one bio signal is measured in each of switching operations.

Second, for the apparatus of FIG. 3, the combining unit 325 combines ACs having m frequencies to then be applied to the sensing unit 340 and m separating units are arranged to separate an AC voltage having each frequency component from the AC voltage detected from the sensing unit 340. According to this, a switching operation of the first and second temporal separating units 230 and 250 is performed twice within one sampling period T1 and the first or second bio signal is measured in each of switching operations. It is required that a frequency band in which each of m first bio signals exists is separated from each other.

FIGS. 4A and 4B show examples of a temporal separating method adopted in the first temporal separating units 130, 230 and 330 and the second temporal separating units 150, 250 and 350 shown in FIGS. 1 through 3. Here, a switching operation is performed twice within one sampling period T1. Referring to FIGS. 4A and 4B, the first bio signal is measured in the Ta period and the second bio signal is measured in the Tb period. In particular, a Td period shown in FIG. 4B is used for discharging the stimulus signal applied to the human body in the Ta period and arranged between the Ta period and the Tb period. The size of the Td period may be empirically obtained through experiments or computer simulations. According to this, after the first bio signal has been measured, the remaining stimulus signal in the human body can be discharged, which results in minimizing interference caused by the stimulus signal during the measurement of the second bio signal. For more effective discharging, a resistor (not shown) and a switch (not shown) connected in series are arranged between the second electrode (E2) of the sensing units 240 and 340 to which the stimulus signal is applied and the ground and the switch is turned on in the Td period. As a result, in the Td period, prompt discharging may be achieved via the resistor. In the present exemplary embodiments, the sampling period is 500 Hz, i.e., 2 ms, but is not limited thereto.

Figure 6:
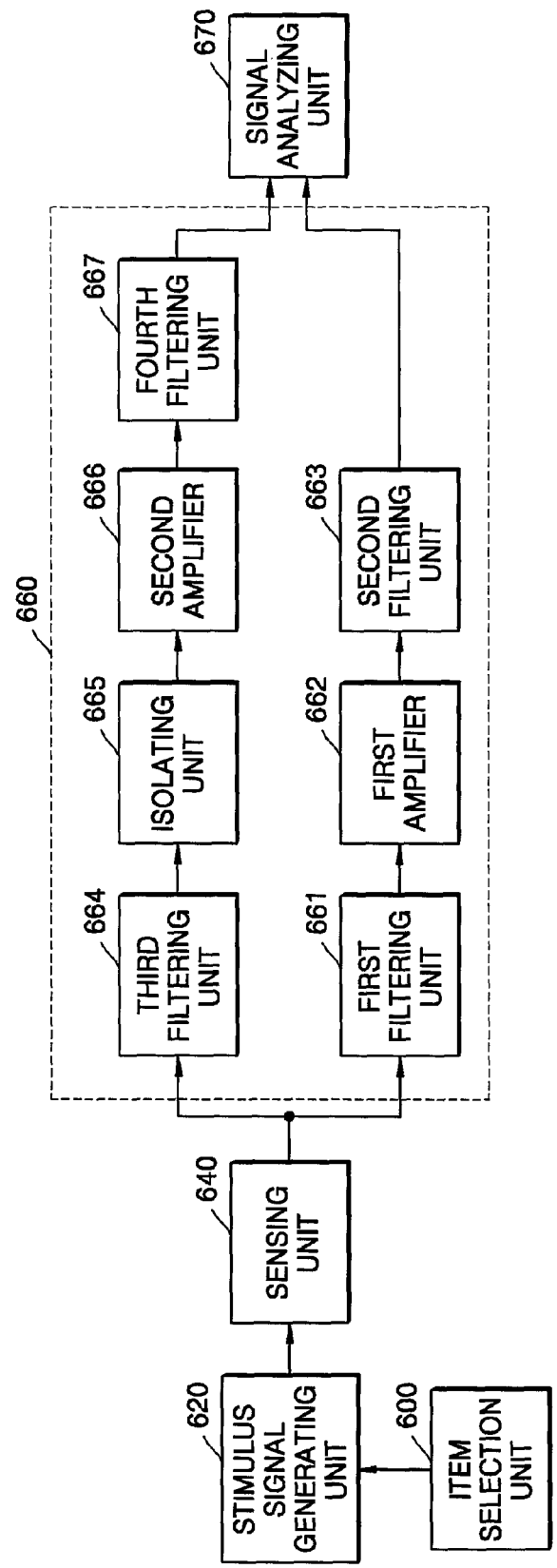
FIG. 6 is a schematic block diagram of a bio signal measurement apparatus according to a second exemplary embodiment of the present invention.

FIG. 6 is a schematic block diagram of a bio signal measurement apparatus according to a second exemplary embodiment of the present invention, which measures the first and second bio signals using the electric separation. The apparatus includes an item selection unit 600, a stimulus signal generating unit 620, a sensing unit 640, a signal acquisition unit 660 and a signal analyzing unit 670. The item selection unit 600 may be optionally included. The signal acquisition unit 660 comprises first and second acquisition units. The first acquisition unit includes a first filtering unit 661, a first amplifier 662 and a second filtering unit 663 and the second acquisition unit includes a third filtering unit 664, an isolating unit 665, a second amplifier 666 and a fourth filtering unit 667. The apparatus of FIG. 6 adopts a different signal acquisition unit 660 instead of the first and second temporal separating units 130 and 150, comparing with the apparatus of FIG. 1. The detailed description of the parts which are the same as those in the apparatus shown in FIG. 1 will be omitted and the different parts will be mainly described. Here, the body fat is used as the first bio signal and the ECG is used as the second bio signal.

Referring to FIG. 6, a stimulus signal for measuring the first bio signal is applied to the first and second electrodes E1 and E2 of the sensing unit 640. When the second electrode sets as a right leg driver (G) of the ECG, voltages detected from the third and fourth electrodes E3 and E4 are provided to both the first filtering unit 661 and the third filtering unit 664.

In the signal acquisition unit 660, the first filtering unit 661 filters a frequency band in which the first bio signal exists from the detected voltages, i.e., an intermediate signal provided from the sensing unit 640. The first amplifier 662 amplifies the intermediate signal provided from the first filtering unit 661. The second filtering unit 663 removes noise components from the intermediate signal provided from the first amplifier 662 to be provided as the first bio signal.

The third filtering unit 664 filters a frequency band in which the second bio signal exists from the detected voltages, i.e., the intermediate signal provided from the sensing unit 640. The isolating unit 665 isolates the stimulus signal contained in the intermediate signal provided from the third filtering unit 664. The isolating unit 665 comprises any one selected from a group of a buffer, a photo coupler and a transformer. The second amplifier 666 amplifies the intermediate signal provided from the isolating unit 665. The fourth filtering unit 667 removes noise components from the intermediate signal provided from the second amplifier 666 to be provided as the second bio signal.

In order to effectively measure the first and second bio signals using the apparatus of FIG. 6, it may be preferable that each frequency band in which the first or the second bio signal exists is separated from each other.

Figure 7:
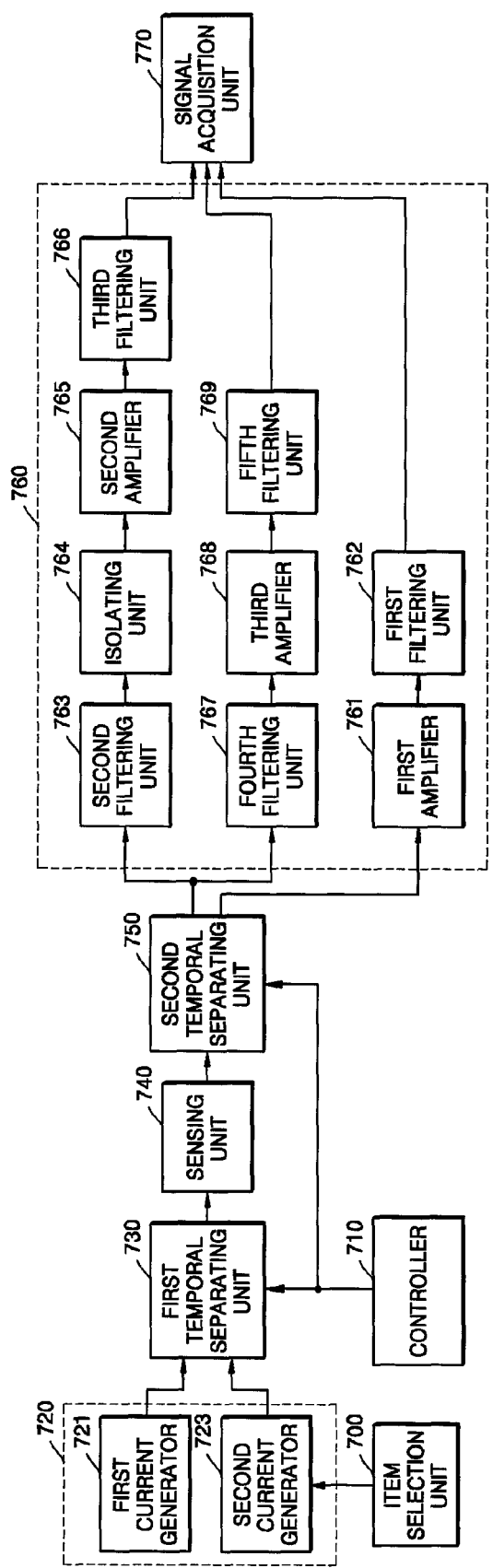
FIG. 7 is a schematic block diagram of a bio signal measurement apparatus according to a third exemplary embodiment of the present invention.

FIG. 7 is a schematic block diagram of a bio signal measurement apparatus according to a third exemplary embodiment of the present invention, which measures the first and second bio signals using both the temporal separation and the electric separation. The apparatus includes an item selection unit 700, a controller 710, a stimulus signal generating unit 720, a first temporal separating unit 730, a sensing unit 740, a second temporal separating unit 750, a signal acquisition unit 760 and a signal analyzing unit 770. The item selection unit 700 may be optionally included. The stimulus signal generating unit 720 comprises first and second current generators 721 and 723. The signal acquisition unit 760 includes first through third acquisition units. The first acquisition unit comprises a first amplifier 761 and a first filtering unit 762. The second acquisition unit comprises a second filtering unit 763, an isolating unit 764, a second amplifier 765 and a third filtering unit 766. The third acquisition unit comprises a fourth filtering unit 767, a third amplifier 768 and a fifth filtering unit 769. The apparatus of FIG. 7 additionally adopts the first and second temporal separating units 730 and 750, comparing with the apparatus of FIG. 6. The detailed description of the parts which are the same as those in the apparatus shown in FIG. 6 will be omitted and the different parts will be mainly described. Here, the body fat is used as the first bio signal and the ECG is used as the second bio signal.

Referring to FIG. 7, the sensing unit 740 comprises a first electrode E1 for applying the first and second stimulus signals and detecting the first intermediate signal, a second electrode E2 for applying the second stimulus signal and used as a right leg driver, a third electrode E3 for applying the first stimulus signal and detecting the first and second intermediate signals, and a fourth electrode E4 for detecting the first and second intermediate signals.

The first temporal separating unit 730 operates in response to the control signal provided from the controller 710 and applies a first stimulus signal in a first interval, i.e., the period of each sampling period and a second stimulus signal in a second interval, i.e., the Tb period of each sampling period, to the human body via the sensing unit 740. The first stimulus signal is used for measuring the skin resistance and the second stimulus signal is used for measuring the body fat.

The second temporal separating unit 750 operates in response to the control signal and provides a first intermediate signal detected from the first and third electrodes E1 and E3 of the sensing unit 740 in the Ta period and a second intermediate signal detected from the third and fourth electrodes E3 and E4 of the sensing unit 740 in the Tb period, to the signal acquisition unit 760.

The signal acquisition unit 760 obtains the first bio signal, i.e., the skin resistance signal from the first intermediate signal using the temporal separation and the first bio signal, i.e., the body fat signal and the second bio signal, i.e., the ECG signal from the second intermediate signal using the filtering and electric separation.

In the signal acquisition unit 760, the first amplifier 761 amplifies the first intermediate signal, i.e., voltages detected from the first and third electrodes E1 and E3 of the sensing unit 740 in the Ta period. The first filtering unit 762 removes noise components from the first intermediate signal provided from the first amplifier 761 to be provided as the first bio signal, i.e., the skin resistance signal.

The second filtering unit 763 filters a frequency band in which the second bio signal, i.e., the ECG signal exists from the second intermediate signal, i.e., voltages detected from the third and fourth electrodes E3 and E4 of the sensing unit 740 in the Tb period. The isolating unit 764 isolates the second stimulus signal contained in the second intermediate signal provided from the second filtering unit 763. The isolating unit 764 comprises any one selected from a group of a buffer having a high input impedance, a photo coupler and a transformer. The second amplifier 765 amplifies the second intermediate signal provided from the isolating unit 764. The third filtering unit 766 removes noise components from the second intermediate signal provided from the second amplifier 765 to be provided as the second bio signal, i.e., the ECG signal.

The fourth filtering unit 767 filters a frequency band in which the first bio signal, i.e., the body fat signal exists from the second intermediate signal, i.e., voltages detected from the third and fourth electrodes E3 and E4 of the sensing unit 740 in the Tb period. The third amplifier 768 amplifies the second intermediate signal provided from the fourth filtering unit 767. The fifth filtering unit 769 removes noise components from the second intermediate signal provided from the third amplifier 768 to be provided as the first bio signal, i.e., the body fat signal.

In the apparatus of FIG. 7, the skin resistance signal whose frequency band is adjacent to that of the ECG signal is separated using the first and second temporal separating unit 730 and 750. Also, the body fat signal and the ECG signal whose frequency bands are separated from each other, obtained through the temporal separation are separated from each other using the second and fourth filtering unit 763 and 767 and the isolating unit 764. As a result, a variety of bio signals can be accurately measured regardless of their frequency bands. In addition, a circuit for removing a jitter may be arranged next to the second temporal separating unit 750. In addition, a circuit for matching impedance may be arranged to compensate for a reduction of impedance caused by the jitter removing circuit.

Figure 8:
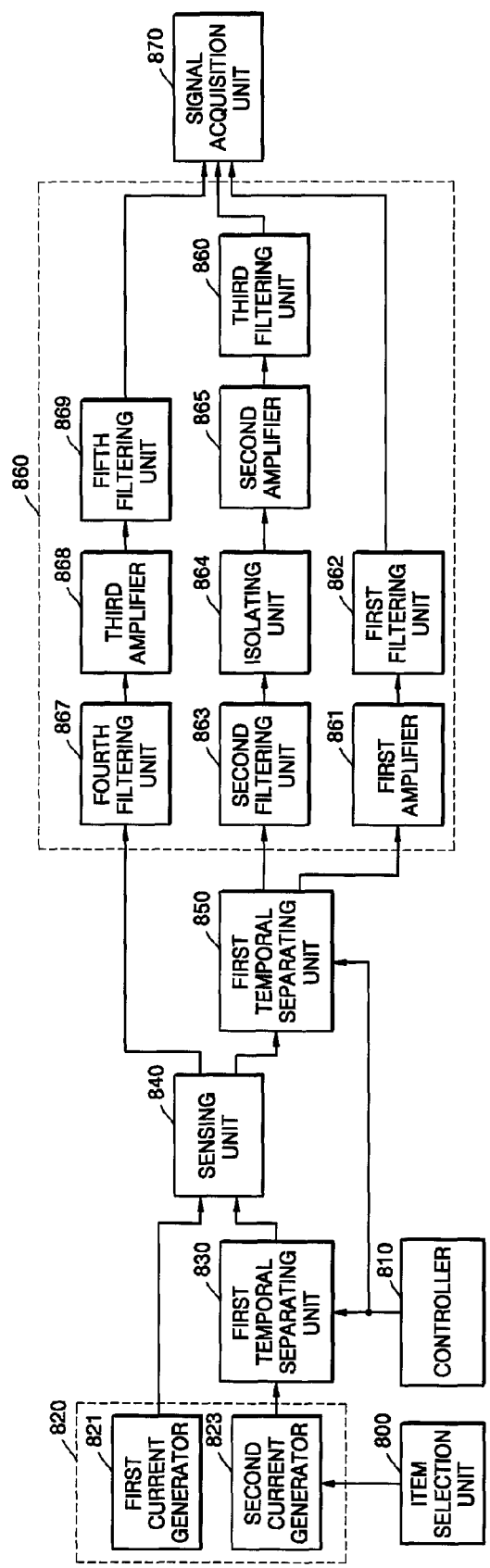
FIG. 8 is a schematic block diagram of a bio signal measurement apparatus according to a fourth exemplary embodiment of the present invention.

FIG. 8 is a schematic block diagram of a bio signal measurement apparatus according to a fourth exemplary embodiment of the present invention, which measures the first and second bio signals using both the temporal separation and the electric separation. The apparatus includes an item selection unit 800, a controller 810, a stimulus signal generating unit 820, a first temporal separating unit 830, a sensing unit 840, a second temporal separating unit 850, a signal acquisition unit 860 and a signal analyzing unit 870. The item selection unit 800 may be optionally included. The stimulus signal generating unit 820 comprises first and second current generators 821 and 823. The signal acquisition unit 860 includes first through third acquisition units. The first acquisition unit comprises a first amplifier 861 and a first filtering unit 862. The second acquisition unit comprises a second filtering unit 863, an isolating unit 864, a second amplifier 865 and a third filtering unit 866. The third acquisition unit comprises a fourth filtering unit 867, a third amplifier 868 and a fifth filtering unit 869. The apparatus of FIG. 8 additionally adopts the first and second temporal separating units 830 and 850 and their locations, comparing with the apparatus of FIGS. 6 and 7. The detailed description of the parts which are the same as those in the apparatus shown in FIGS. 6 and 7 will be omitted and the different parts will be mainly described. Here, the body fat is represented by the first bio signal and the ECG is represented by the second bio signal.

Referring to FIG. 8, the sensing unit 840 comprises a first electrode E1 for applying the first and second stimulus signals and detecting the first intermediate signal, a second electrode E2 for applying the second stimulus signal and used as a right leg driver, a third electrode E3 for applying the first stimulus signal and detecting the first and second intermediate signals, and a fourth electrode E4 for detecting the first and second intermediate signals.

The first temporal separating unit 830 operates in response to the control signal provided from the controller 810 and applies a first stimulus signal to the human body via the sensing unit 840 in a first interval, i.e., the Ta period of each sampling period. The first stimulus signal is used for measuring the skin resistance.

The second temporal separating unit 850 operates in response to the control signal and provides a first intermediate signal detected from the third and fourth electrodes E3 and E4 of the sensing unit 840 in the Ta period and a second intermediate signal detected from the third and fourth electrodes E3 and E4 of the sensing unit 840 in the Tb period of the sampling period to the signal acquisition unit 860.

Here, a second stimulus signal used for measuring the body fat is applied to the human body via the sensing unit 840 regardless of periods. The third intermediate signal is detected from the third and fourth electrodes E3 and E4 of the sensing unit 840 regardless of periods.

The signal acquisition unit 860 obtains the body fat signal using the filtering and the skin resistance and the ECG signal using the temporal separation and the skin resistance signal.

In the signal acquisition unit 860, the first amplifier 861 amplifies the first intermediate signal, i.e., voltages detected from the first and third electrodes E1 and E3 of the sensing unit 840 in the Ta period. The first filtering unit 862 removes noise components from the first intermediate signal provided from the first amplifier 861 to be provided as the first bio signal, i.e., the skin resistance signal.

The second filtering unit 863 filters a frequency band in which the second bio signal, i.e., the ECG signal, exists from the second intermediate signal, i.e., voltages detected from the third and fourth electrodes E3 and E4 of the sensing unit 840 in the Tb period. The isolating unit 864 isolates the second stimulus signal contained in the second intermediate signal provided from the second filtering unit 863. The isolating unit 864 comprises any one selected from a group of a buffer having a high input impedance, a photo coupler and a transformer. The second amplifier 865 amplifies the second intermediate signal provided from the isolating unit 864. The third filtering unit 866 removes noise components from the second intermediate signal provided from the second amplifier 865 to be provided as the second bio signal, i.e., the ECG signal.

The fourth filtering unit 867 filters a frequency band in which the first bio signal, i.e., the body fat signal exists from the third intermediate signal, i.e., voltages detected from the third and fourth electrodes E3 and E4 of the sensing unit 740 regardless of periods. The third amplifier 868 amplifies the third intermediate signal provided from the fourth filtering unit 867. The fifth filtering unit 869 removes noise components from the second intermediate signal provided from the third amplifier 868 to be provided as the first bio signal, i.e., the body fat signal.

A component (not shown) for measuring third bio signals such as blood sugar by irradiating light of a specific wavelength as an external stimulus can be added to the bio signal measurement apparatuses according to the present invention.

For the bio signal measurement apparatuses according to the exemplary embodiments, the item selection unit 100 and the controller 110 can be substituted by a signal stimulus signal generating unit 120 generating predetermined ACs of a different specific frequency and the first and second switching units 130 and 150 can be automatically switched every predetermined time in a rotary motor shape. In this case, it may be preferable that the signal analyzing unit 170 analyzes signals provided by the signal acquisition unit 160 after a stabilizing duration for a predetermined time.

In the bio signal measurement apparatuses according to the exemplary embodiments, the stimulus signal for the first bio signals are not definitely limited to the AC. For example, any one of AC and direct current (DC) can be used for measuring the skin resistance. Therefore, when two first bio signals, such as the body fat signal and the skin resistance signal are measured at the same time, without the combining unit 323, an AC having a specific frequency for measuring the body fat and a DC for measuring the skin resistance are applied to the sensing unit 340, and thus an AC voltage having the specific frequency and a DC voltage can be separated from a signal sensed by the sensing unit 340 as the first bio signal for the body fat and the first bio signal for the skin resistance.

Figure 9:
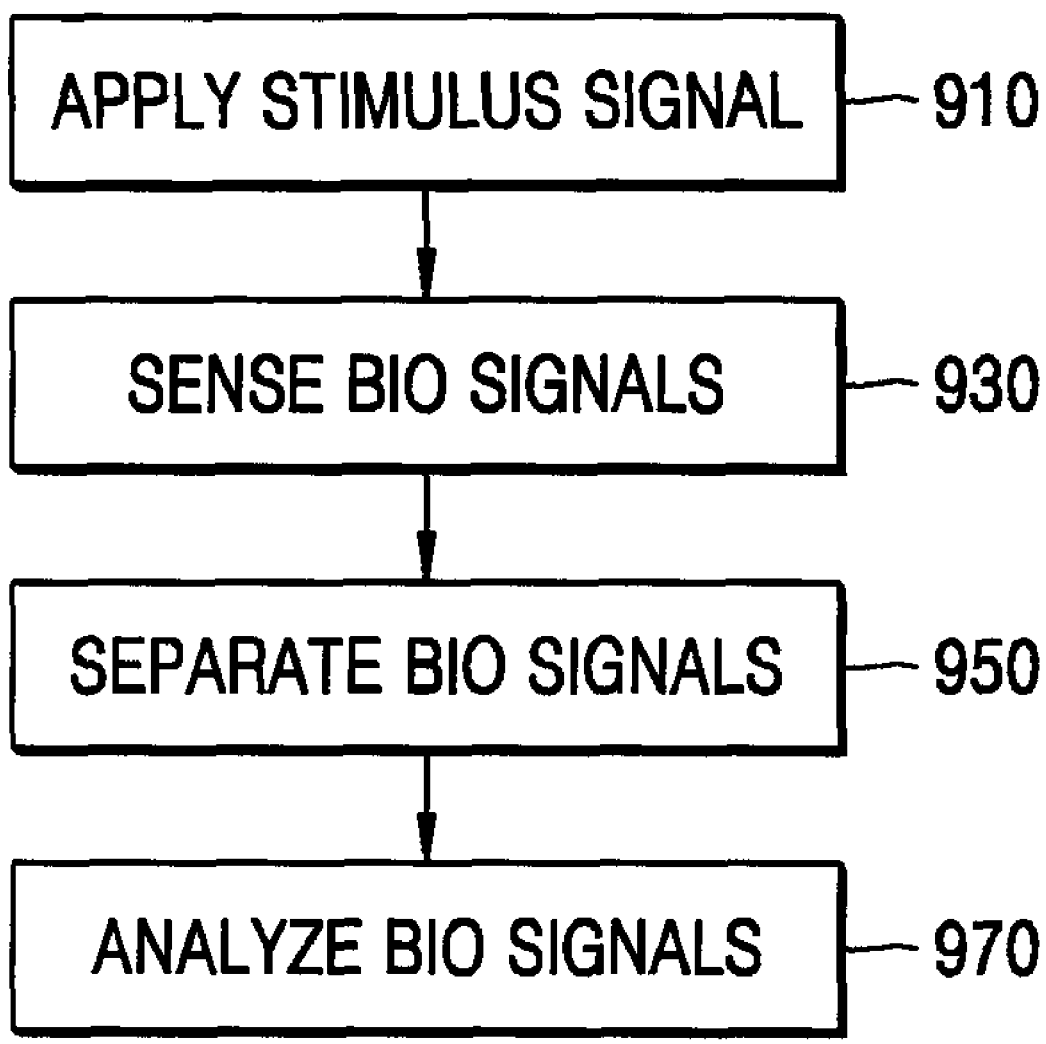
FIG. 9 is a flowchart of a bio signal measurement method according to a fifth exemplary embodiment of the present invention.

FIG. 9 is a flowchart of a bio signal measurement method according to still a fifth exemplary embodiment of the present invention.

Referring to FIG. 9, in operation 910, when a user attaches the sensing unit 140 included in the measurement apparatus to a specific region of a human body, a stimulus signal, e.g., an AC of a predetermined frequency, is applied to the sensing unit 140. Methods of applying the stimulus signal can be largely divided into five categories. First, in a case where one kind of the first bio signals and one kind of the second bio signals are measured, an AC of a predetermined frequency is applied in every Ta of a sampling period, as shown in FIG. 2. Second, in a case where one kind of the first bio signals and at least two kinds of the second bio signals are measured, at least two ACs having a different frequency are combined, and the combined ACs are applied in every Ta period of a sampling period, as shown in FIG. 3. Third, an AC of a predetermined frequency is consistently applied irrespective of the Ta and Tb periods of a sampling period, as shown in FIG. 6. Fourth, an AC of a first frequency is applied in every Ta of a sampling period and an AC of a second frequency is applied in every Tb of the sampling period, as shown in FIG. 7. Fifth, an AC of a first frequency is applied in every Ta of a sampling period and an AC of a second frequency is consistently applied irrespective of the Ta and Tb periods of the sampling period, as shown in FIG. 8.

In operation 930, intermediate signals for obtaining bio signals are sensed from the sensing unit 140. To detect the intermediate signals, a connection among the electrodes shown in FIGS. 2 and 3 and its modified connection can be used.

In operation 950, the first and the second bio signals are separated from the intermediate signals detected in operation 930. To separate the first and the second bio signals, at least one of the temporal separation and the electric separation can be used, as shown in FIGS. 2, 3 and 6 through 8.

In operation 970, the items are analyzed by inputting the first and the second bio signals separated in operation 950, and data for each item is generated as the analysis results.

The exemplary embodiments of the present invention can be written as computer programs and can be implemented in general-use digital computers that execute the programs using a computer-readable recording medium. Examples of the computer-readable recording medium include magnetic storage media (e.g., ROM, floppy disks, hard disks, etc.), optical recording media (e.g., CD-ROMs, DVDs, etc.), and storage media such as carrier waves (e.g., transmission through the internet). The computer-readable recording medium can also be distributed over network coupled computer systems so that the computer-readable code is stored and executed in a distributed fashion. And the functional programs, codes and code segments for embodying the present invention may be easily deducted by programmers in the art which the present invention belongs to.

As described above, according to exemplary embodiments of the present invention, since at least two bio signals having different physical mechanisms can be measured, with at least one electrode in a sensing unit shared to apply the stimulus signal or to detect each bio signal, a user can easily and timely acquire the desired bio signals, and even if more bio signals have to be measured, the time required for measuring all the bio signals can be greatly reduced.

In addition, various kinds of bio signals can be simultaneously measured without interference by using at least one of temporal separating and electric separating, thereby being capable of integrating into one measurement apparatus. Therefore, cost reduction can be expected, and a user operation is simple.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A bio signal measurement apparatus for simultaneously measuring a first bio signal generated by a human body in response to a stimulus signal and a second bio signal naturally generated by the human body, the apparatus comprising:

a stimulus signal generating unit which is configured to generate the stimulus signal to be applied to the human body;

a sensing unit which is adapted to contact the human body and includes a plurality of electrodes to which the stimulus signal is applied, the plurality of electrodes detecting at least one intermediate signal containing the first and second bio signals from the human body that occur simultaneously, and the sensing unit being configured to share at least one of the plurality of electrodes to apply the stimulus signal to the human body and to detect the at least one intermediate signal including the first bio signal and the second bio signal; a signal acquisition unit which is configured to acquire the detected at least one intermediate signal and to separate the first bio signal and the second bio signal from the at least one intermediate signal detected from the sensing unit;

a first temporal separating unit which is configured to operate in response to a control signal and to apply a first stimulus signal in a first interval of each sampling period and a second stimulus signal in a second interval of each sampling period, to the human body via the sensing unit;

a second temporal separating unit which is configured to operate in response to the control signal and to provide a first intermediate signal detected by the sensing unit in the first interval and a second intermediate signal detected by the sensing unit in the second interval, to the signal acquisition unit; and wherein the signal acquisition unit comprises:

a first acquisition unit which is configured to obtain the first bio signal from a first intermediate signal detected from the sensing unit; and a second acquisition unit which is configured to electrically separate and obtain the second bio signal from a second intermediate signal detected by the sensing unit, wherein the second acquisition unit comprises:

a filtering unit which is configured to filter a frequency band in which the second bio signal exists from the second intermediate signal; and an isolating unit which is configured to isolate the stimulus signal contained in the second intermediate signal which is filtered.

2. The apparatus of claim 1, wherein the isolating unit comprises one of a buffer, a photo coupler and a transformer.

3. A bio signal measurement apparatus for simultaneously measuring a first bio signal generated by a human body in response to a stimulus signal and a second bio signal naturally generated by the human body, the apparatus comprising:

a stimulus signal generating unit which is configured to generate the stimulus signal to be applied to the human body;

a sensing unit which is adapted to contact the human body and includes a plurality of electrodes to which the stimulus signal is applied, the plurality of electrodes detecting at least one intermediate signal containing the first and second bio signals from the human body that occur simultaneously, and the sensing unit being configured to share at least one of the plurality of electrodes to apply the stimulus signal to the human body and to detect the at least one intermediate signal including the first bio signal and the second bio signal; and a signal acquisition unit which is configure to acquire the detected at least one intermediate signal and to separate the first bio signal and the second bio signal from the at least one intermediate signal detected from the sensing unit, the apparatus further comprising:

a first temporal separating unit which is configured to operate in response to a control signal and applies a first stimulus signal in a first interval of each sampling period and a second stimulus signal in a second interval of each sampling period, to the human body via the sensing unit;

a second temporal separating unit which is configured to operate in response to the control signal and provides a first intermediate signal detected by the sensing unit in the first interval and a second intermediate signal detected by the sensing unit in the second interval, to the signal acquisition unit; and a controller which is configured to generate the control signal, wherein the signal acquisition unit obtains the first bio signal from the first and second intermediate signals and obtains the second bio signal by electrically separating the second intermediate signal.

4. The apparatus of claim 3, wherein the signal acquisition unit:

a filtering unit which is configured to filter a frequency band in which the second bio signal exists from the second intermediate signal; and an isolating unit which is configured to isolate the second stimulus signal contained in the second intermediate signal which is filtered.

5. The apparatus of claim 4, wherein the isolating unit comprises one of a buffer, a photo coupler and a transformer.

6. A bio signal measurement apparatus for simultaneously measuring a first bio signal generated by a human body in response to a stimulus signal and a second bio signal naturally generated by the human body, the apparatus comprising:

a stimulus signal generating unit which is configured to generate the stimulus signal to be applied to the human body;

a sensing unit which is adapted to contact the human body and includes a plurality of electrodes to which the stimulus signal is applied, the plurality of electrodes detecting at least one intermediate signal containing the first and second bio signals from the human body that occur simultaneously, and the sensing unit being configured to share at least one of the plurality of electrodes to apply the stimulus signal to the human body and to detect the at least one intermediate signal including the first bio signal and the second bio signal; and a signal acquisition unit which is configured to acquire the detected at least one intermediate signal and separates the first bio signal and the second bio signal from the at least one intermediate signal detected from the sensing unit, the apparatus further comprising:

a first temporal separating unit which is configured to operate in response to a control signal and to apply a first stimulus signal to the human body via the sensing unit in a first interval of each sampling period;

a second temporal separating unit which is configured to operate in response to the control signal and to provide a first intermediate signal detected by the sensing unit in the first interval and a second intermediate signal detected by the sensing unit in a second interval of each sampling period to the signal acquisition unit; and a controller which is configured to generate the control signal, wherein a second stimulus signal is applied to the human body via the sensing unit in the first and second intervals to detect a third intermediate signal from the sensing unit, and the signal acquisition unit obtains the first bio signal from the first and third intermediate signals and obtains the second bio signal by electrically separating the second intermediate signal.

7. The apparatus of claim 6, wherein the signal acquisition unit:

a filtering unit which is configured to filter a frequency band in which the second bio signal exists from the second intermediate signal; and an isolating unit which is configured to isolate the second stimulus signal contained in the second intermediate signal which is filtered.

8. The apparatus of claim 7, wherein the isolating unit comprises one of a buffer, a photo coupler and a transformer.

9. A bio signal measurement apparatus for simultaneously measuring a first bio signal generated by a human body in response to a stimulus signal and a second bio signal naturally generated by the human body, the apparatus comprising:

a stimulus signal generating unit which is configured to generate the stimulus signal to be applied to the human body;

a sensing unit which is adapted to contact the human body and includes a plurality of electrodes to which the stimulus signal is applied, the plurality of electrodes detecting at least one intermediate signal containing the first and second bio signals from the human body that occur simultaneously, and the sensing unit being configured to share at least one of the plurality of electrodes to apply the stimulus signal to the human body and to detect the at least one intermediate signal including the first bio signal and the second bio signal; and a signal acquisition unit which is configured to acquire the detected at least one intermediate signal and to separate the first bio signal and the second bio signal from the at least one intermediate signal detected from the sensing unit, the apparatus further comprising:

a first temporal separating unit which is configured to operate in response to a control signal and applies first and second stimulus signals to the human body via the sensing unit in a first interval of a sampling period of a pulse signal for detecting the at least one intermediate signal;

a second temporal separating unit which is configured to operate in response to the control signal and to provide a first intermediate signal detected by the sensing unit in the first interval and a second intermediate signal detected by the sensing unit in a second interval of the sampling period to the signal acquisition unit; and a controller which is configured to generate the control signal, wherein the signal acquisition units obtains two first bio signals from the first intermediate signal using first and second frequencies, respectively and obtains the second bio signal from the second intermediate signal.

10. The apparatus of claim 9, wherein the stimulus signal generating unit comprises:

a first current generator which is configured to generate current of a first frequency to be used as the first stimulus signal;

a second current generator which is configured to generate current of a second frequency to be used as the second stimulus signal; and a combining unit which is configured to combine the first and second stimulus signals.

11. The apparatus of claim 9, wherein the sampling period includes a third interval for discharging interposed between the first interval and the second interval.

12. The apparatus of claim 11 further comprising a resistor which is configured to externally discharge the first and second stimulus signals remaining in the human body, in the third interval.

13. A bio signal measurement method of simultaneously measuring a first bio signal generated by a human body in response to a stimulus signal and a second bio signal naturally generated in the human body, the method comprising:

providing a sensing unit adapted to contact the human body, including a plurality of electrodes to which the stimulus signal is applied, the plurality of electrodes detecting at least one intermediate signal containing the first and second bio signals from the human body that occur simultaneously, and configured to share at least one of the plurality of electrodes to apply the stimulus signal to the human body and to detect the at least one intermediate signal including the first bio signal and the second bio signal;

generating the stimulus signal to be applied to the human body; and acquiring the detected at least one intermediate signal and separating the first bio signal and the second bio signal from the at least one intermediate signal detected by the sensing unit, the method further comprising:

applying a first stimulus signal in a first interval of each sampling period and a second stimulus signal in a second interval of each sampling period, to the human body, in response to a control signal; and generating a first intermediate signal detected by the sensing unit in the first interval and a second intermediate signal detected by the sensing unit in the second interval, in response to the control signal, wherein the first bio signal is obtained from the first and second intermediate signals and the second bio signal is obtained by electrically separating the second intermediate signal.

14. A bio signal measurement method of simultaneously measuring a first bio signal generated by a human body in response to a stimulus signal and a second bio signal naturally generated in the human body, the method comprising:

providing a sensing unit adapted to contact the human body, including a plurality of electrodes to which the stimulus signal is applied, the plurality of electrodes detecting at least one intermediate signal containing the first and second bio signals from the human body that occur simultaneously, and configured to share at least one of the plurality of electrodes to apply the stimulus signal to the human body and to detect the at least one intermediate signal including the first bio signal and the second bio signal;

generating the stimulus signal to be applied to the human body; and acquiring the detected at least one intermediate signal and separating the first bio signal and the second bio signal from the at least one intermediate signal detected by the sensing unit, the method further comprising:

applying a first stimulus signal to the human body via the sensing unit in a first interval of each sampling period, in response to a control signal; and providing a first intermediate signal detected by the sensing unit in the first interval and a second intermediate signal detected by the sensing unit in a second interval of each sampling period, in response to the control signal, wherein a second stimulus signal is applied to the human body via the sensing unit in the first and second intervals to detect a third intermediate signal from the sensing unit, and the first bio signal is obtained from the first and third intermediate signals and the second bio signal is obtained by electrically separating the second intermediate signal.

15. A bio signal measurement method of simultaneously measuring a first bio signal generated by a human body in response to a stimulus signal and a second bio signal naturally generated in the human body, the method comprising:

providing a sensing unit adapted to contact the human body, including a plurality of electrodes to which the stimulus signal is applied, the plurality of electrodes detecting at least one intermediate signal containing the first and second bio signals from the human body that occur simultaneously, and configured to share at least one of the plurality of electrodes to apply the stimulus signal to the human body and to detect the at least one intermediate signal including the first bio signal and the second bio signal;

generating the stimulus signal to be applied to the human body; and acquiring the detected at least one intermediate signal and separating the first bio signal and the second bio signal from the at least one intermediate signal detected by the sensing unit, the method further comprising:

applying a first and a second stimulus signal to the human body via the sensing unit in a first interval of each sampling period, in response to a control signal; and providing a first intermediate signal detected by the sensing unit in the first interval and a second intermediate signal detected by the sensing unit in a second interval of each sampling period, in response to the control signal, wherein two first bio signals are obtained from the first intermediate signal the using a first and a second frequency, respectively, and the second bio signal is obtained from the second intermediate signal.

16. The method of claim 15, wherein each sampling period includes a third interval for discharging between the first interval and the second interval.

17. A non-transitory computer-readable recording medium having recorded thereon a computer-readable program for performing a bio signal measurement method of simultaneously measuring a first bio signal generated by a human body in response to a stimulus signal and a second bio signal naturally generated by the human body, the method comprising:

detecting at least one intermediate signal containing the first and second bio signals from the human body that occurs simultaneously, by using a sensing unit adapted to contact the human body, including a plurality of electrodes to which the stimulus signal is applied, the plurality of electrodes detecting the at least one intermediate signal containing the first and second bio signals from the human body that occurs simultaneously, and configured to share at least one of the plurality of electrodes to apply the stimulus signal to the human body and to detect the at least one intermediate signal including the first bio signal and the second bio signal;

generating the stimulus signal to be applied to the human body; and acquiring the detected at least one intermediate signal and separating the first bio signal and the second bio signal from the at least one intermediate signal detected by the sensing unit, wherein the acquiring and separating the first and second bio signals comprises:

applying a first stimulus signal in a first interval of each sampling period and a second stimulus signal in a second interval of each sampling period to the human body via the sensing unit in response to a control signal;

generating a first intermediate signal detected by the sensing unit in the first interval and a second intermediate signal detected by the sensing unit in the second interval;

obtaining the first bio signal from the first intermediate signal detected by the sensing unit; and electrically separating and obtaining the second bio signal from the second intermediate signal detected by the sensing unit, wherein the electrically separating and obtaining the second bio signal further comprises:

filtering a frequency band in which the second bio signal exists from the second intermediate signal; and isolating the second stimulus signal contained in the second intermediate signal which is filtered.

18. A non-transitory computer-readable recording medium having recorded thereon a computer-readable program for performing a bio signal measurement method of simultaneously measuring a first bio signal generated by a human body in response to a stimulus signal and a second bio signal naturally generated by the human body, the method comprising:

detecting at least one intermediate signal containing the first and second bio signals from the human body that occurs simultaneously, by using a sensing unit adapted to contact the human body, including a plurality of electrodes to which the stimulus signal is applied, the plurality of electrodes detecting the at least one intermediate signal containing the first and second bio signals from the human body that occurs simultaneously, and configured to share at least one of the plurality of electrodes to apply the stimulus signal to the human body and to detect the at least one intermediate signal including the first bio signal and the second bio signal;

generating the stimulus signal to be applied to the human body; and acquiring the detected at least one intermediate signal and separating the first bio signal and the second bio signal from the at least one intermediate signal detected by the sensing unit, wherein the method further comprises:

applying a first stimulus signal in a first interval of each sampling period and a second stimulus signal in a second interval of each sampling period, to the human body, in response to a control signal; and providing a first intermediate signal detected by the sensing unit in the first interval and a second intermediate signal detected by the sensing unit in the second interval, in response to the control signal, wherein the first bio signal is obtained from the first and second intermediate signals and the second bio signal is obtained by electrically separating the second intermediate signal.

19. A non-transitory computer-readable recording medium having recorded thereon a computer-readable program for performing a bio signal measurement method of simultaneously measuring a first bio signal generated by a human body in response to a stimulus signal and a second bio signal naturally generated by the human body, the method comprising:

detecting at least one intermediate signal containing the first and second bio signals from the human body that occurs simultaneously, by using a sensing unit adapted to contact the human body, including a plurality of electrodes to which the stimulus signal is applied, the plurality of electrodes detecting the at least one intermediate signal containing the first and second bio signals from the human body that occurs simultaneously, and configured to share at least one of the plurality of electrodes to apply the stimulus signal to the human body and to detect the at least one intermediate signal including the first bio signal and the second bio signal;

generating the stimulus signal to be applied to the human body; and acquiring the detected at least one intermediate signal and separating the first bio signal and the second bio signal from the at least one intermediate signal detected by the sensing unit, wherein the method further comprises:

applying a first stimulus signal to the human body via the sensing unit in a first interval of each sampling period, in response to a control signal; and providing a first intermediate signal detected by the sensing unit in the first interval and a second intermediate signal detected by the sensing unit in a second interval of each sampling period, in response to the control signal, wherein a second stimulus signal is applied to the human body via the sensing unit in the first and second intervals to detect a third intermediate signal from the sensing unit, and the first bio signal is obtained from the first and third intermediate signals and the second bio signal is obtained by electrically separating the second intermediate signal.

20. A non-transitory computer-readable recording medium having recorded thereon a computer-readable program for performing a bio signal measurement method of simultaneously measuring a first bio signal generated by a human body in response to a stimulus signal and a second bio signal naturally generated by the human body, the method comprising:
- detecting at least one intermediate signal containing the first and second bio signals from the human body that occurs simultaneously, by using a sensing unit adapted to contact the human body, including a plurality of electrodes to which the stimulus signal is applied, the plurality of electrodes detecting the at least one intermediate signal containing the first and second bio signals from the human body that occurs simultaneously, and configured to share at least one of the plurality of electrodes to apply the stimulus signal to the human body and to detect the at least one intermediate signal including the first bio signal and the second bio signal;
- generating the stimulus signal to be applied to the human body; and
- acquiring the detected at least one intermediate signal and separating the first bio signal and the second bio signal from the at least one intermediate signal detected by the sensing unit, wherein the method further comprises:

applying a first and a second stimulus signal to the human body via the sensing unit in a first interval of each sampling period, in response to a control signal; and providing a first intermediate signal detected by the sensing unit in the first interval and a second intermediate signal detected by the sensing unit in a second interval of each sampling period, in response to the control signal, wherein two first bio signals are obtained from the first intermediate signal using a first and a second frequency, respectively, and the second bio signal is obtained from the second intermediate signal.

* * * * *